(12) United States Patent
Muraoka et al.

(10) Patent No.: US 8,859,294 B2
(45) Date of Patent: Oct. 14, 2014

(54) METHOD FOR BINDING A PROTEIN CONSISTING OF PROTEIN A OR CONSISTING OF AT LEAST ONE DOMAIN OF THE A TO E DOMAINS OF THE PROTEIN A TO THE SUBSTRATE

(75) Inventors: Jin Muraoka, Osaka (JP); Takachika Azuma, Chiba (JP); Akikazu Murakami, Chiba (JP)

(73) Assignee: Panasonic Corporation, Osaka (JP)

( * ) Notice: Subject to any disclaimer, the term of this patent is extended or adjusted under 35 U.S.C. 154(b) by 33 days.

(21) Appl. No.: 13/074,973

(22) Filed: Mar. 29, 2011

(65) Prior Publication Data

US 2011/0229982 A1   Sep. 22, 2011

Related U.S. Application Data

(63) Continuation of application No. PCT/JP2010/007116, filed on Dec. 7, 2010.

(30) Foreign Application Priority Data

Mar. 17, 2010   (JP) ................................ 2010-060587

(51) Int. Cl.
*G01N 33/68* (2006.01)
*C07K 17/14* (2006.01)
*C07K 14/31* (2006.01)
*C07K 17/02* (2006.01)
*C07K 7/06* (2006.01)

(52) U.S. Cl.
CPC ........... *C07K 17/14* (2013.01); *C07K 2319/705* (2013.01); *C07K 7/06* (2013.01)
USPC ........ 436/501; 435/283.1; 530/350; 530/402; 530/409; 530/410

(58) Field of Classification Search
None
See application file for complete search history.

(56) References Cited

U.S. PATENT DOCUMENTS

| | | | |
|---|---|---|---|
| 4,946,778 A * | 8/1990 | Ladner et al. ................ | 435/69.6 |
| 6,399,750 B1 * | 6/2002 | Johansson ..................... | 530/413 |
| 2006/0134805 A1 | 6/2006 | Berg et al. | |
| 2006/0257394 A1 | 11/2006 | Humprheys et al. | |
| 2010/0048876 A1 | 2/2010 | Hall et al. | |

FOREIGN PATENT DOCUMENTS

| | | |
|---|---|---|
| JP | 2006-170617 | 6/2006 |
| JP | 2006-317401 | 11/2006 |
| JP | 2007-536898 | 12/2007 |
| JP | 2008-523140 | 7/2008 |
| JP | 2010-504754 | 2/2010 |

OTHER PUBLICATIONS

BIACORE Application Note 9, dated Feb. 2002.*
Mikio Kato et al., "Formation of Interchain Disulfide Bonds in Bence Jones Proteins and Fab(t) Fragments of Immunoglobulin G Through Thiol-Disulfide Interchange," J. Biochem. vol. 84, No. 6, 1978. pp. 1475-1483.
Rusmini, F., et al.: "Protein Immobilization Strategies for Protein Biochips", Biomacromolecules 2007, vol. 8, No. 6, pp. 1775-1789.
Chinese Search Report issued in corresponding Chinese Application No. 201080003763.1, dated Oct. 14, 2013, 2 pages.

* cited by examiner

*Primary Examiner* — Galina Yakovleva
(74) *Attorney, Agent, or Firm* — McDermott Will & Emery LLP

(57) ABSTRACT

The object of the present invention is to provide a method for immobilizing the SpA protein on the surface of a substrate with high density without causing dimerization.
The following method solves the object. That is, the method for binding a protein to a surface of a substrate, comprising steps (A) to (B): step (A) of preparing said protein to the surface, step (B) of supplying said protein to the surface, wherein said protein consists of a Protein A or at least one domain of A to E of said Protein A, and said protein comprises C-terminal modified amino acid sequence represented by SEQ ID:1(SFNRSEC).

8 Claims, 12 Drawing Sheets

← A

| temperature | time | cycle number |
|---|---|---|
| 95 (°C) | 2 (min) | 1 |
| 96 (°C) | 30 (sec) | 35 |
| 52 (°C) | 30 (sec) | |
| 72 (°C) | 30 (sec) | |
| 72 (°C) | 4 (min) | 1 |
| 4 (°C) | keep | |

| 6×His | D domain | SFNRNEC |

| 6xHis | D domain | C |

Fig. 14
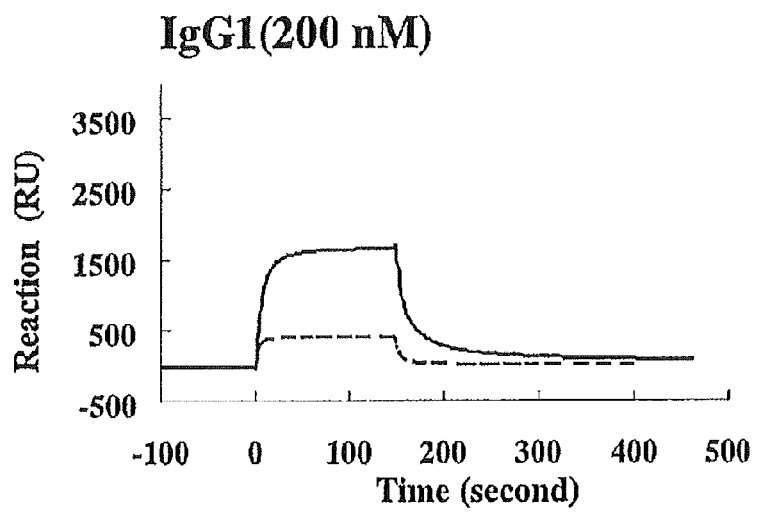
Fig. 15
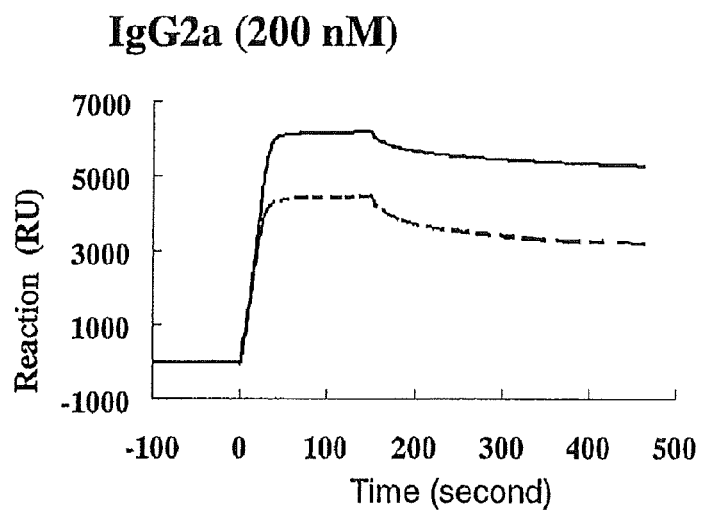
Fig. 16
| 6xHis | E domain | D domain | A domain | B domain | C domain | SFNRNEC |

METHOD FOR BINDING A PROTEIN CONSISTING OF PROTEIN A OR CONSISTING OF AT LEAST ONE DOMAIN OF THE A TO E DOMAINS OF THE PROTEIN A TO THE SUBSTRATE

CROSS-REFERENCE TO RELATED APPLICATION

This is a continuation of PCT International Application PCT/JP2010/007116 filed on Dec. 7, 2010, claiming priority from Japanese Patent Application No. 2010-060587, filed on Mar. 17, 2010, the disclosures of which applications are hereby incorporated by reference herein.

SEQUENCE LISTING

The Sequence listing in "SEQUENCE LISTING.TXT" created on May 19, 2011, being 3.98 KB in size is incorporated by reference.

TECHNICAL FIELD

This invention relates to a method for binding a protein consisting of Protein A or consisting of at least one domain of the A to E domains of the Protein A to the surface of a substrate.

BACKGROUND ART

Protein A is a protein which constitutes five percent of the cell wall of *staphylococcus aureus* and is abbreviated as "SpA". The Protein A is consisting of five domains of A to E domains and doesn't contain cysteine.

A protein consisting of the Protein A or at least one domain of the A to E domains (hereinafter, "SpA protein") has a property of being able to bind to an antibody. Utilizing this property, the Spa Protein is used to bind the antibody to a substrate.

According to a prior art, a lysine residue contained in the Spa Protein is bound to the carboxyl group on the substrate with use of amine-coupling method.

CITATION LIST

Patent Literature

[PTL 1]
Japanese laid-open patent publication No. 2006-170617

Non-Patent Literature

[NPL 1]
J. Biochem. 84, 1475-1483 (1978)

SUMMARY OF INVENTION

Technical Problem

The Spa Protein immobilized with use of the prior art has low density on the surface of the substrate, because the Spa Protein has a plurality of the lysine residues, and has no orientation on the surface of the substrate.

Incidentally, according to a known method, R—SH (R represents hydrocarbon group) is absorbed on the surface of a gold substrate to form an oriented membrane represented by the chemical formula: Au—S—R. In order to bind the SpA protein to a gold substrate with the method, it is considered that cysteine is bound to the terminal of the SpA protein.

However, when C-terminal of the SpA protein is modified with cystein ($NH_2$—CH(COOH)$CH_2$—SH), dimerization of the spA protein is caused in the solution containing the SpA Protein. As shown in the following formula (I), mercapto groups (—SH) in the cysteins polymerize each other, thus a disulfide bond is formed.

[Chem. 1]

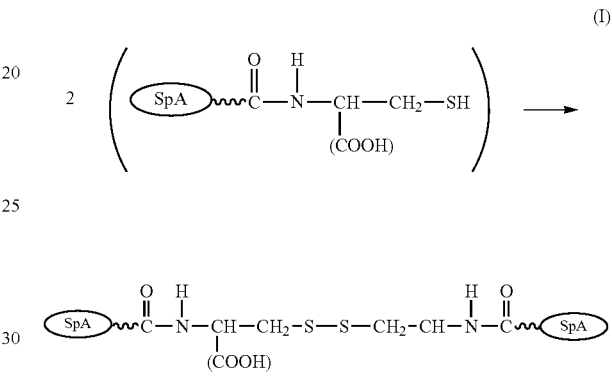

(wherein SpA represents the SpA protein.)

The dimerization inhibits the SpA proteins from being immobilized on the substrate.

The present inventors have discovered that the SpA protein having the C-terminal modified with SEQ ID:1 (SFNRNEC), which contains cystein, is immobilized with high orientation on the surface of the substrate.

The purpose of the present invention is to provide a method for immobilizing the SpA protein on the surface of a substrate in high density without causing dimerization.

Solution to Problem

The following method solves the above problem(s).

[1]: A method for binding a protein to a surface of a substrate, comprising the following steps (A) to (B):

Step (A) of preparing said substrate with the surface comprising gold or a carboxyl group, and Step (B) of supplying said protein to the surface, wherein said protein consists of a Protein A or at least one domain of A to E domain of said Protein A, and said protein comprises C-terminal modified with an amino acid sequence represented by SEQ ID:1(SFNRNEC)

[2]: The method described in above [1], wherein said surface comprises gold.

[3]: The method described in above [1], wherein said surface comprises a carboxyl group, and said surface is bound to said protein according to the following chemical formula (III):

[Chem.3]

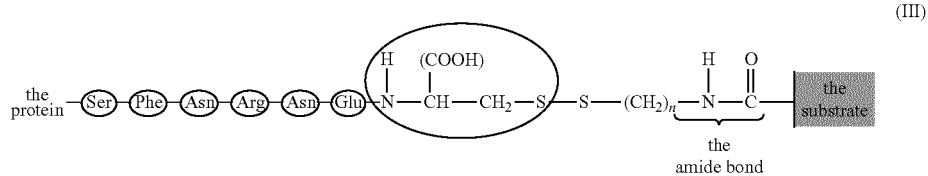

(III)

the amide bond (wherein n denotes a natural number.)

[4]: The method described in above [1], further comprising the following steps (C) to (D) in this order between the Step A and the Step B:

Step (C) of supplying a solution containing 1-ethyl-3-(3-Dimethylaminopropyl) carbodiimide HCl or equivalent thereof and N-Hydroxysuccinimide to the surface, and

[Chem.2]

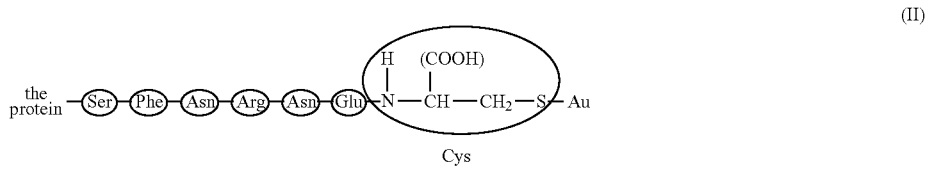

(II)

Cys

[Chem.3]

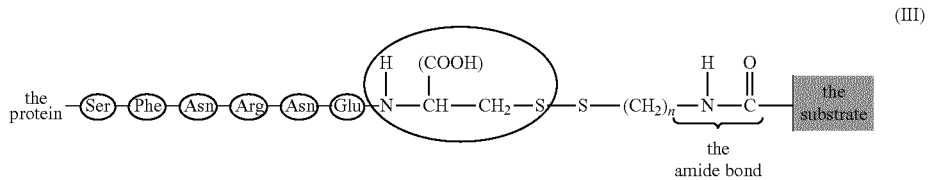

(III)

the amide bond

Step (D) of supplying a compound represented by following formula (IV) to the surface.

[Chem.4]

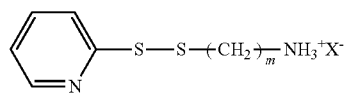

(IV)

(wherein m denotes a natural number, X represents an halogen atom.)

[5]: The method described above [4], wherein m in the formula (IV) is a natural number within the range of 2 to 20.

[6]: The method described in above [5], wherein m in the formula (IV) is 2.

[7]: The method described in above [1], wherein said protein consists of at least one domain of A to E domain of said Protein A.

[8]: The method described in above [7], wherein said protein consists of a D domain of said Protein A.

[9]: The method described in [7], wherein said protein consists of said Protein A.

[10]: A substrate with a surface in which a protein is immobilized, wherein:

said substrate comprises gold or an amide bond, said protein consists of a Protein A or at least one domain of A to E domain of said Protein A, and said protein comprises C-terminal modified with an amino acid sequence represented by SEQ ID: 1(SFNRNEC)

[11]: The substrate described in above [10], wherein said protein is immobilized according to the following chemical formula (II) or (III):

(wherein n denotes a natural number.)

[12]: The substrate described in above [11], wherein said protein is immobilized according to the chemical formula (II).

[13]: The substrate described in above [11], wherein said protein is immobilized according to the chemical formula (III).

[14]: The substrate described in [10], wherein said protein consists of at least one domain of A to E domain of said Protein A.

[15]: The substrate described in above [14], wherein said protein consists of a D domain of said Protein A.

[16]: The substrate described in above [14], wherein said protein consists of said Protein A.

[17]: An aqueous solution containing a protein, wherein:

said protein consists of a Protein A or at least one domain of A to E domain of said Protein A, and said protein comprises C-terminal modified with an amino acid sequence represented by SEQ ID:1(SFNRNEC)

[18]: A protein, wherein:

said protein consists of a Protein A or at least one domain of A to E domain of said Protein A, and said protein comprises C-terminal modified with an amino acid sequence represented by SEQ ID:1(SFNRNEC).

Advantageous Effect of the Invention

The present invention provides a method for immobilizing the SpA protein on the surface of the substrate in high density without causing dimerization.

BRIEF DESCRIPTION OF DRAWINGS

FIG. 9 shows a schematic view of the SF-modified D domain with the N-terminal modified with 6×His.
FIG. 10 shows a schematic view of the C-modified D domain with the N-terminal modified with 6×His.
FIG. 14 shows a graph showing the measurement results of the immobilization amounts of the C-modified D domain and the SF-modified D domain.
FIG. 15 shows a graph showing the measurement results of the immobilization amounts of the C-modified D domain and the SF-modified D domain.
FIG. 16 shows a schematic view of Protein A, which contains all the A to E domains.

DESCRIPTION OF EMBODIMENTS

Definition of Terms

Figure 1:
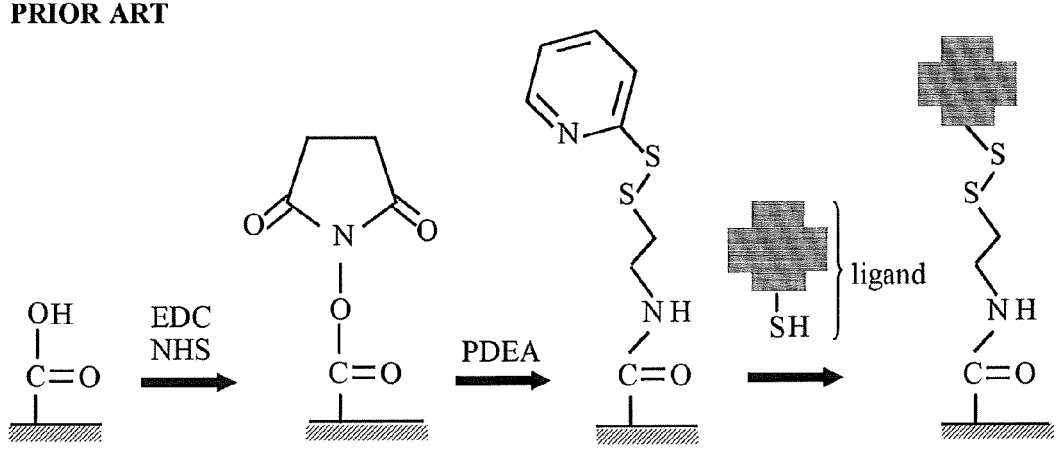
FIG. 1 shows thiol-coupling method.

The terms used in the present specification are defined as below.
The term "Protein A" is a protein which constitutes five percent of the cell wall of *staphylococcus aureus* and is abbreviated as "SpA". The Protein A is consisting of five domains of A to E domains and doesn't contain cysteine.

The term "SpA protein" means a protein consisting of Protein A or at least one domain of A to E domains of Protein A. Namely, the term "SpA protein" means Protein A, the A domain of Protein A, the B domain of Protein A, the C domain of Protein A, the D domain of Protein A, the E domain of Protein A, and the combination of at least two of the A to E domains.

The term "SF-modified SpA protein" means a SpA protein with the C-terminal modified with SEQ:ID 1(SFNRNEC).

The term "SF-modified D domain" means a protein consisting of a D domain with the C-terminal modified with SEQ:ID 1(SFNRNEC).

The term "SF-modified D domain gene" means a gene in which the gene coding SEQ ID:1 (SFNRNEC) is modified at the C-terminal of the gene coding the D domain of Protein A.

The term "Nde1-XhoI-SD-modified D domain gene" means the SF-modified D domain gene in which restriction enzyme sites Nde1 and XhoI are modified at the N-terminal and the C-terminal thereof, respectively.

The term "C-modified domain" means a protein consisting of a D domain with the C-terminal modified with cysteine.

The term "SF-modified SpA" means a protein consisting of Protein A with the C-terminal modified with SEQ ID:1(SFNRNEC)

The term "C-modified SpA" means a protein consisting of Protein A with the C-terminal modified with cysteine.

(Step (A))
In step (A), a substrate with a surface comprising gold or carboxyl groups is prepared.

A substrate with a surface comprising gold includes not only a substrate comprising gold on the surface thereof, but also a substrate comprising gold only on the portion where the Spa proteins are to be immobilized. Specifically, the substrate comprises a thin film composed of gold or a fine particle composed of gold.

Similar to in the case of gold, a substrate comprising a carboxyl group includes not only a substrate in which a thin film comprising a carboxyl group is formed on the surface thereof, but also a substrate comprising carboxyl group only on the portion where the Spa proteins are to be immobilized. Specifically, the substrate comprises a thin film comprising a carboxyl group on the surface thereof.

(Step (B))
In step (B), an SF-modified SpA protein is supplied to the surface of the substrate.

In the case where the substrate comprises gold on the surface thereof, the SF-modified SpA protein is immobilized on the surface of the substrate, as shown in the following chemical formula (II).

[Chem.2]

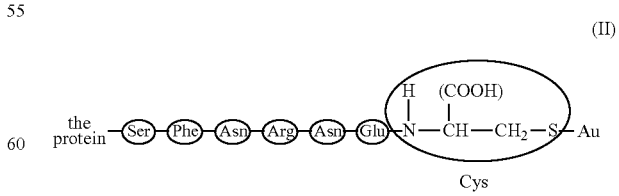

(II)

In the case where the substrate comprises a carboxyl group on the surface thereof, the SF-modified SpA proteins are immobilized on the surface of the substrate with thiol-coupling, as shown in the following chemical formula (III).

[Chem.3]

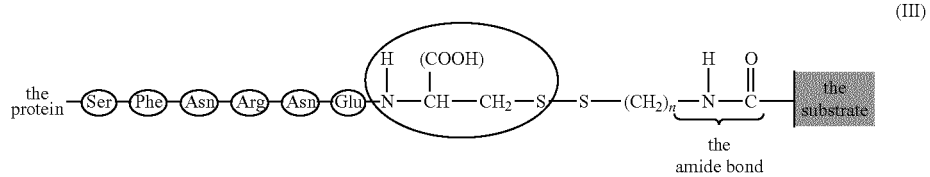

(III)

the amide bond (wherein n denotes a natural number.)

FIG. 1 shows a thiol-coupling method. A mixture of EDC/NHS is supplied to the surface comprising a carboxyl group. EDC represents N-ethyl-N'-(3-dimethylaminopropyl) carbodiimide chloride and the equivalent thereof. As the equivalent thereof, hydro halogenides such as hydrofluoride, hydriodide and hydrobromate are exemplified. NHS is the abbreviated name of N-hydroxysuccinimide.

Subsequently, PDEA is supplied. PDEA is the abbreviated name of 2-(2-pyridinyldithio)ethaneamine hydrochloride.

Finally, a ligand having a mercapto group (—SH) is supplied.

In the present invention, SF-modified SpA protein is supplied as the ligand.

Instead of PDEA, a compound represented by the following formula (IV) can be also used.

[Chem.4]

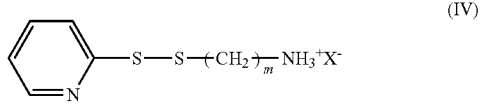

(IV)

(wherein m denotes a natural number, X represents a halogen atom.)

Preferably, a natural number m is selected from within a range from 2 to 20.

Because the immobilized SF-modified SpA protein has high orientation, the SF-modified SpA protein has high density on the surface of the substrate.

Example 1

Preparation of Gene (Vector)

(Vector to Confirm Formation of SF-Modified D Domain Gene and Preparation of Vector to Express SF-Modified D Domain Gene)

Figure 2:
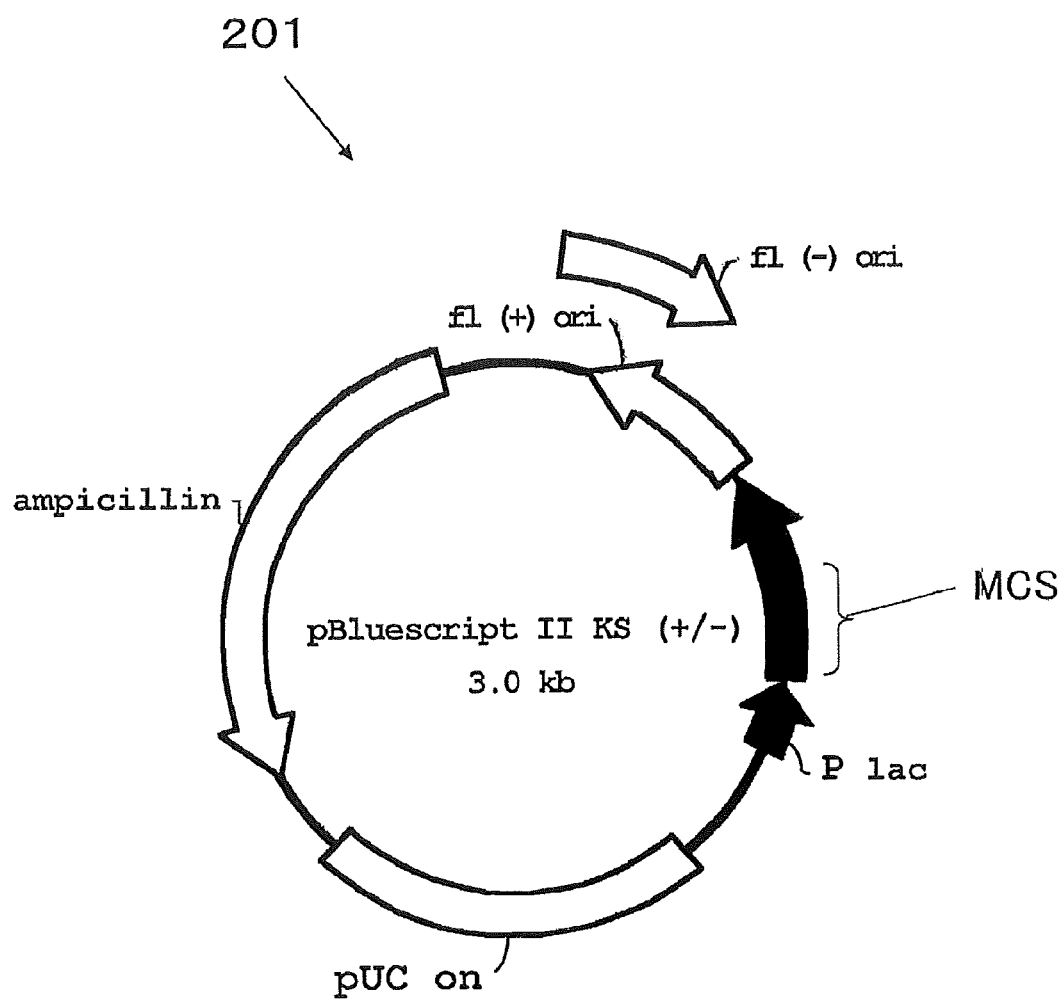
FIG. 2 shows a schematic view of the cloning vector 201.
Figure 3:
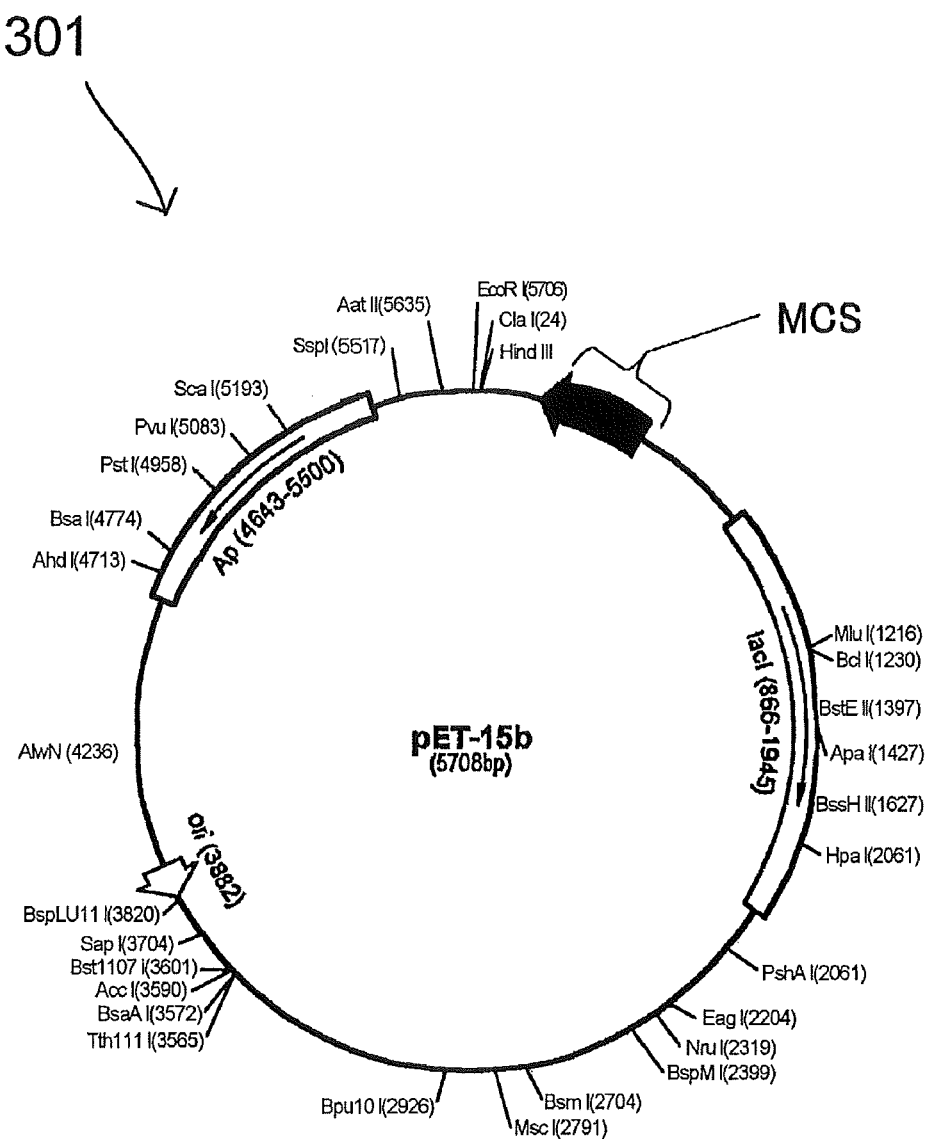
FIG. 3 shows a schematic view of the vector 301.

FIG. 2 and FIG. 3 show a cloning vector 201 to confirm the formation of a SF-modified D domain and a vector 301 to express an SF-modified D domain gene with a E. coli, respectively.

Both the vector 201 and the vector 301 are circular. Both the cloning vector 201 and the vector 301 have a multi cloning site (hereinafter, "MCS") to where the SF-modified D domain gene can be introduced.

The MCS has a restriction enzyme site. With the use of a restriction enzyme, the SF-modified D domain can be introduced into the MCS. An example of the cloning vector 201 and the vector 301 are pBluescript II SK(+) (stratagene) and pET15b(Novagen Inc.) respectively. The pBluescript II is used for the confirmation and growth of the SF-modified D domain gene introduced into the MCS. pET15b is used for the production of the SF-modified D domain.

The specific procedures are described below.

(Designation and Preparation of D Domain of SpA Protein Having the Amino Acid Sequence of SFNRNEC)

The D domain of Protein A derived from *staphyloccocus aureus* was used as the SF-modified D domain.

Figure 4:
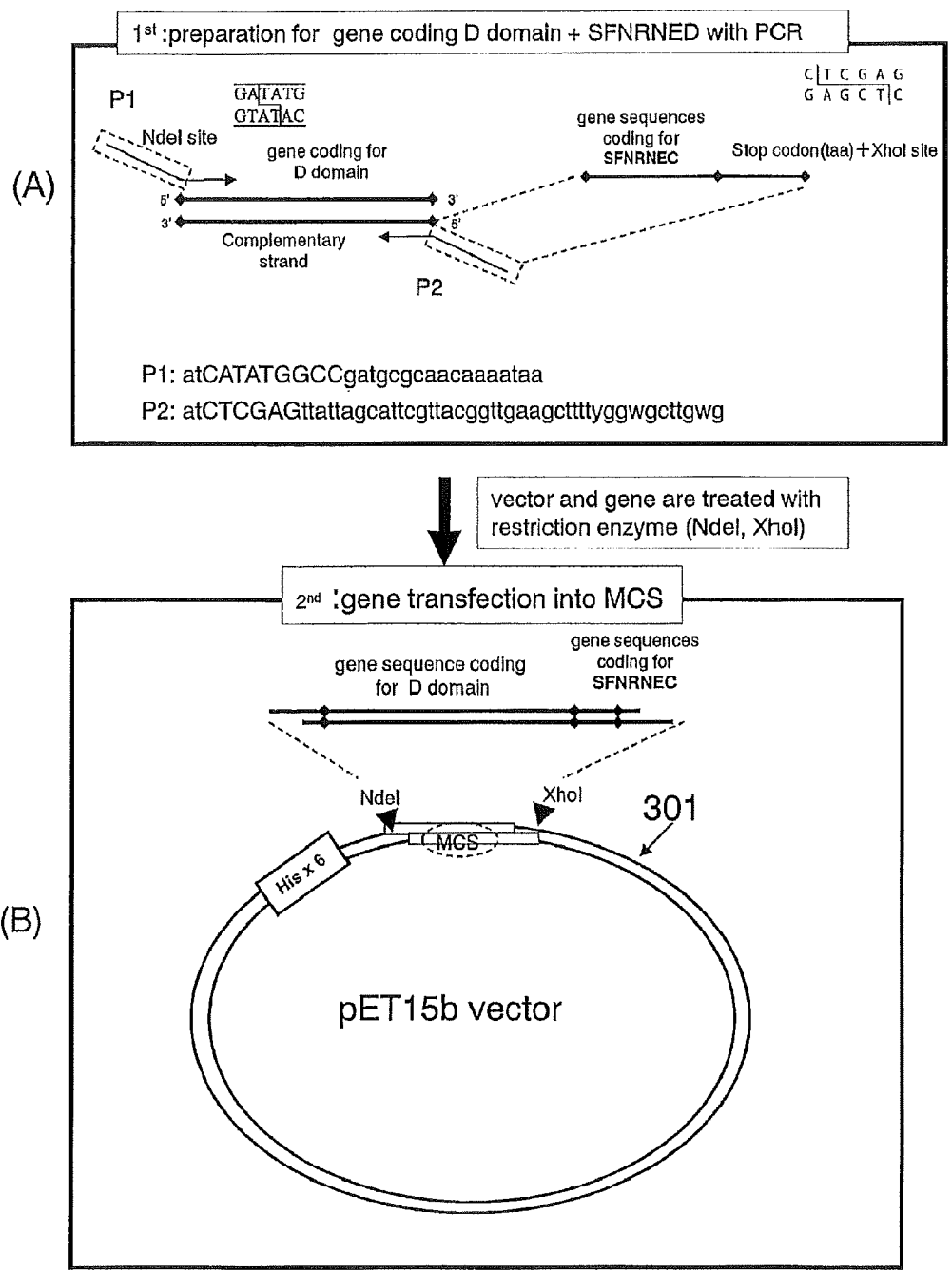
FIG. 4(A) shows a method for modifying the gene coding for SEQ:ID 1 at the C-terminal of the gene coding for the D domain.
FIG. 4(B) shows a method for ligating the gene coding the D domain and SEQ ID:1 to the vector 301.

The gene sequence coding for SEQ:ID 1(SFNRNEC) was added to C-terminal of gene coding for the D domain as shown in FIG. 4(A).

The gene sequence coding for the D domain is described below. gctgatgcgcaacaaaataacttcaa- caaagatcaacaaagcgccttctatgaaatcttgaacatgccta- acttaaacgaagcgcaacgtaac ggcttcattcaaagtcttaaagacgac- ccaagccaaagcactaacgttttaggt- gaagctaaaaaattaaacgaatctcaagcaccgaaa (hereinafter, "SEQ ID:2")

The gene sequence coding for SEQ:ID 1(SFNRNEC) was agcttcaaccgtaacgaatgc (hereinafter, "SEQ ID:3").

As shown in FIG. 4(A), PCR was performed with the use of the primer P1 (SEQ ID:4) in which the gene coding for the restriction enzyme site Nde1 was modified at its N-terminal, and the primer P2 (SEQ ID:5) which codes for SEQ:ID 2-translational stop codon-restriction enzyme site XhoI to obtain the Nde1-XhoI-SF-modified D domain gene, in which the restriction enzyme sites Nde1 and XhoI were modified at the N-terminal and C-terminal thereof, respectively. The following table I shows the profile of the temperature and the time in the PCR.

TABLE I

| temperature | time | cycle number |
|---|---|---|
| 94 (° C.) | 1 (min) | 1 |
| 98 (° C.) | 10 (sec) | 30 |
| 55 (° C.) | 5 (sec) | |
| 72 (° C.) | 30 (sec) | |
| 72 (° C.) | 4 (min) | 1 |
| 4 (° C.) | | keep |

After the PCR, the solution containing the amplified cloning vector 201 was subjected to electrophoresis with 2.0% agarose gel.

Figures 5, 6:
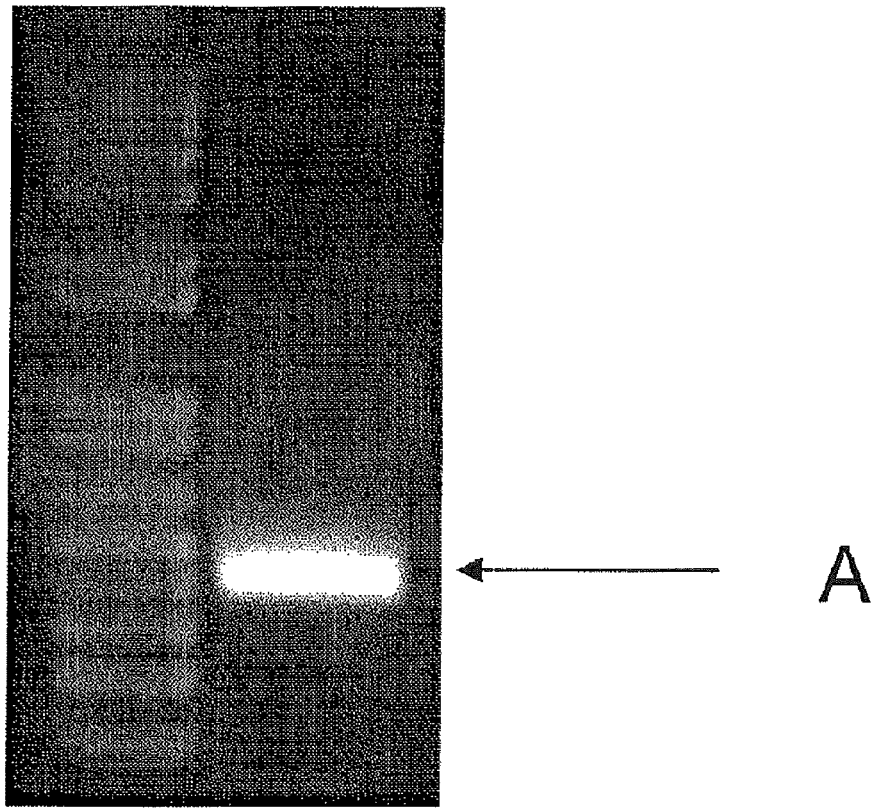
FIG. 5 is a photograph of the electrophoresis showing the amplification of the Nde1-XhoI-SF-modified D domain gene.
FIG. 6 shows the profile of the temperature and the time in the colony PCR.

FIG. 5 is a photograph of the results of the electrophoresis. As shown in FIG. 5, a band was discovered in "A" which indicates approximately 400 bp. This reveals that the Nde1-XhoI-SF-modified D domain gene was amplified.

(Transformation into *E. Coli* and Confirmation of Gene Sequence)

The band shown in FIG. 5 was cut out with the use of WizardSV kit (available from Promega).

The terminal of the Nde1-XhoI-SF-modified D domain gene contained in the band was phosphorylated at a temperature of 37° C. for two hours with T4 Polynucleotide Kinase (available from TOYOBO CO., LTD).

The phosphorylated NdeI-XhoI-SF-modified D domain gene was ligated into the restriction enzyme site EcoRV (MCS) in the cloning vector 201, to introduce the NdeI-XhoI-SF-modified D domain gene into the MCS of p Bluescript II SK(+). The cloning vector 201 was the pBluescriptII SK(+) which was dephosphrylated after assimilation with EcoRV.

The ligation was performed at a temperature of 16° C. for 30 minutes with the use of Ligation High (available from TOYOBO CO. LTD.).

The resulted cloning vector 201 was transformed with the electroporation method using *E. coli* DH10B (trade name: Micro Pulser, available from BioRad company, Program: Ecol). In the electroporation method, the cloning vector 201 at a amount of 0.2 μg and the *E. coli* DH10B at a volume of 42 μL was mixed, and a cuvette with 1 mm Gap was used.

An *E. coli* colony was grown on the LB plate culture media (100 ug/ml ampicillin). A blue white selection was performed. By confirming with a colony PCR, the colony in which the pBluescript II SK(+) was transduced was extracted.

Figure 7:
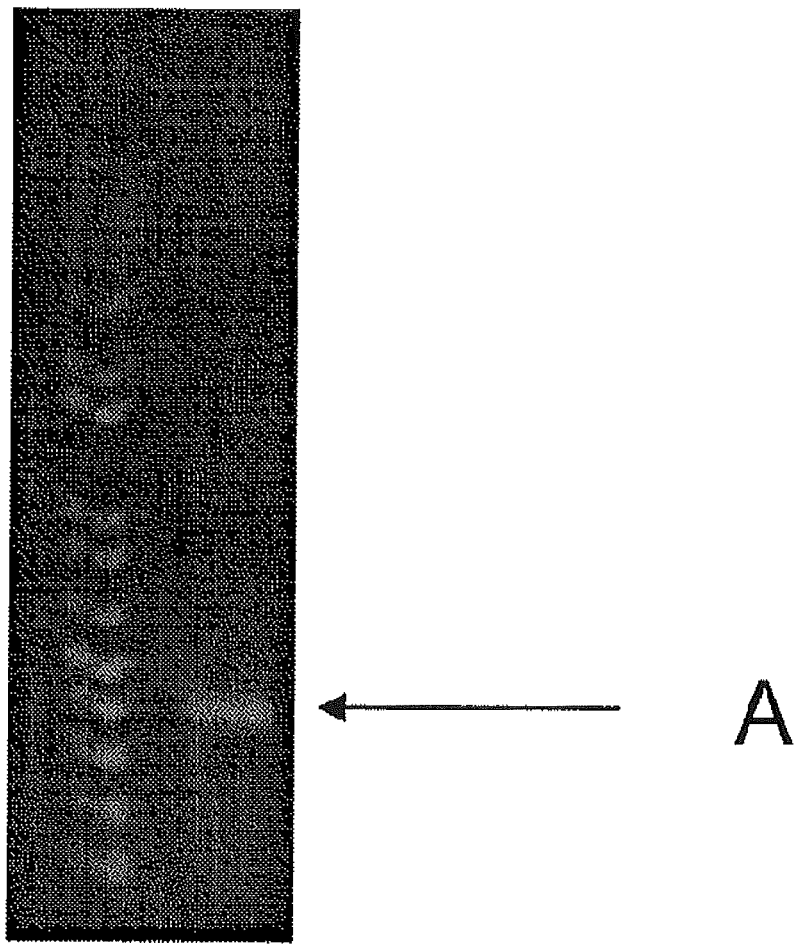
FIG. 7 is a photograph of the electrophoresis showing the amplification of the cloning vector 201 in which the Nde1-XhoI-SF-modified D domain gene is transducted.

FIG. 6 and FIG. 7 show the profile of the temperature and the time of the colony PCR and the result of the electrophoresis, respectively. As shown in FIG. 7, a band was disclosed in "A" which indicates approximately 400 bp. This means that the cloning vector 203 into which the NdeI-XhoI-SF-modified D domain gene was transduced was amplified.

A transduced colony was collected with tip portion of a pipette. The transduced colony was added into an LB culture media (100 ug/ml ampicillin) of approximately 5 to 10 mL. Subsequently, the *E. coli* was grown overnight with oscillation (37° C., 230 rpm). The grown *E. coli* was collected with centrifugation. The collected *E. coli* was purified with the use of miniprep (available from QIAGEN Co., LTD) to obtain plasmid vector 201 comprising NdeI-XhoI-SF-modified D domain gene. Furthermore, the sequence of the resultant plasmid vector 201 was read to confirm the introduced gene sequence.

(Production of Protein)
(Transformation to *E. coli* for Protein Expression)

The SF-modified D domain gene was cut out from the resultant plasmid vector 201 and introduced into MCS of the vector 301.

Specifically, with the use of NdeI (available from Takara Bio Inc) and XhoI (available from Takara Bio Inc.) both of which were restriction enzymes, the resultant plasmid vector 201 was incubated in H buffer (available from Takara Bio Inc.) at a temperature of 37° C. for two hours to cut off the SF-modified D domain gene. The restriction enzyme at an amount of 2 μL was used with regard to the plasmid vector 201 at an amount of 10 μg.

Next, the SF-modified D domain gene was transduced into the vector 301, which was composed of *E. coli* BL21(DE3) pLysS to obtain the *E. coli* colony. Performed was the transduction substantially identical to the transduction of the cloning vector 201.

Specifically, first, SF-modified D domain gene at an amount of approximately 0.2 μg and vector 301 at a volume of 42 μL were mixed. Then, transduction was performed with use of electroporation method (trade name: Micro Pulser, available from BioRad company, Program: Ecol), using a cuvette with 2 mm Gap. Thus, the vector 301 comprising the SF-modified D domain gene was obtained.

Next, the resultant vector 301 was added to LB plate culture media (100 ug/ml ampicillin, 25 ug/mL Chloramphenicol) to grow *E. Coli* colonies on the LB plate culture media.

The resultant *E. coli* colonies were added to 50 mL of 2YT culture media (100 ug/ml ampicillin, 25 ug/mL Chloramphenicol). Subsequently, the *E. coli* BL21(DE3)pLysS was amplified overnight with oscillation at a temperature of 37° C.

The amplified *E. coli* BL21(DE3)pLysS (5 mL) was added to 500 mL of 2YT culture media (100 ug/ml ampicillin). Subsequently, the *E. coli* BL21(DE3)pLysS was incubated at a temperature of 37° C. for one and half hours with oscillation. Finally, IPTG (isopropyl beta-D-1-thiogalacto pyranoside) was added so that the final concentration thereof was 1 mM, and *E. coli* BL21(DE3)pLysS was incubated sufficiently for six hours.

(Purification and Confirmation of SF-Modified D Domain)

The amplified BL21(DE3)pLysS was collected with centrifugation. The collected BL21(DE3)pLysS was suspended again in PBS (pH:7.4) containing imidazole (40 mL) with final concentration of 5 mM. Next, the fungus body was subjected to ultrasonic fragmentation with sonication.

Undissolved fraction was removed with centrifugation, and the residual liquid was passed through the filter of 22 μm. The residual liquid was passed twice through the column filled with the Ni beads (GE healthcare) of a Bed Volume of 0.5 mL, and washed five times with sonication buffer. Four fractions each at a volume of 1 ml were eluted with PBS (pH:7.4) containing imidazole with final concentration of 300 mM. A Protein-eluted fraction was identified from the absorbance of O.D. 280.

It was confirmed that 10 mg of the SF-modified D domain was obtained from the molar molecule absorption coefficient calculated from the absorbance of O.D. 280, molecular weight of the protein, and number of Trp/Tyr. The N-terminal of the SF-modified D domain comprised hexameric histidine (herein after called "6×His").

Furthermore, SDS-PAGE was performed with 16% acrylamide gel to verify how the protein was purified. As reference number 803 in FIG. 8 indicates, the protein was purified with high purity.

Figure 8:
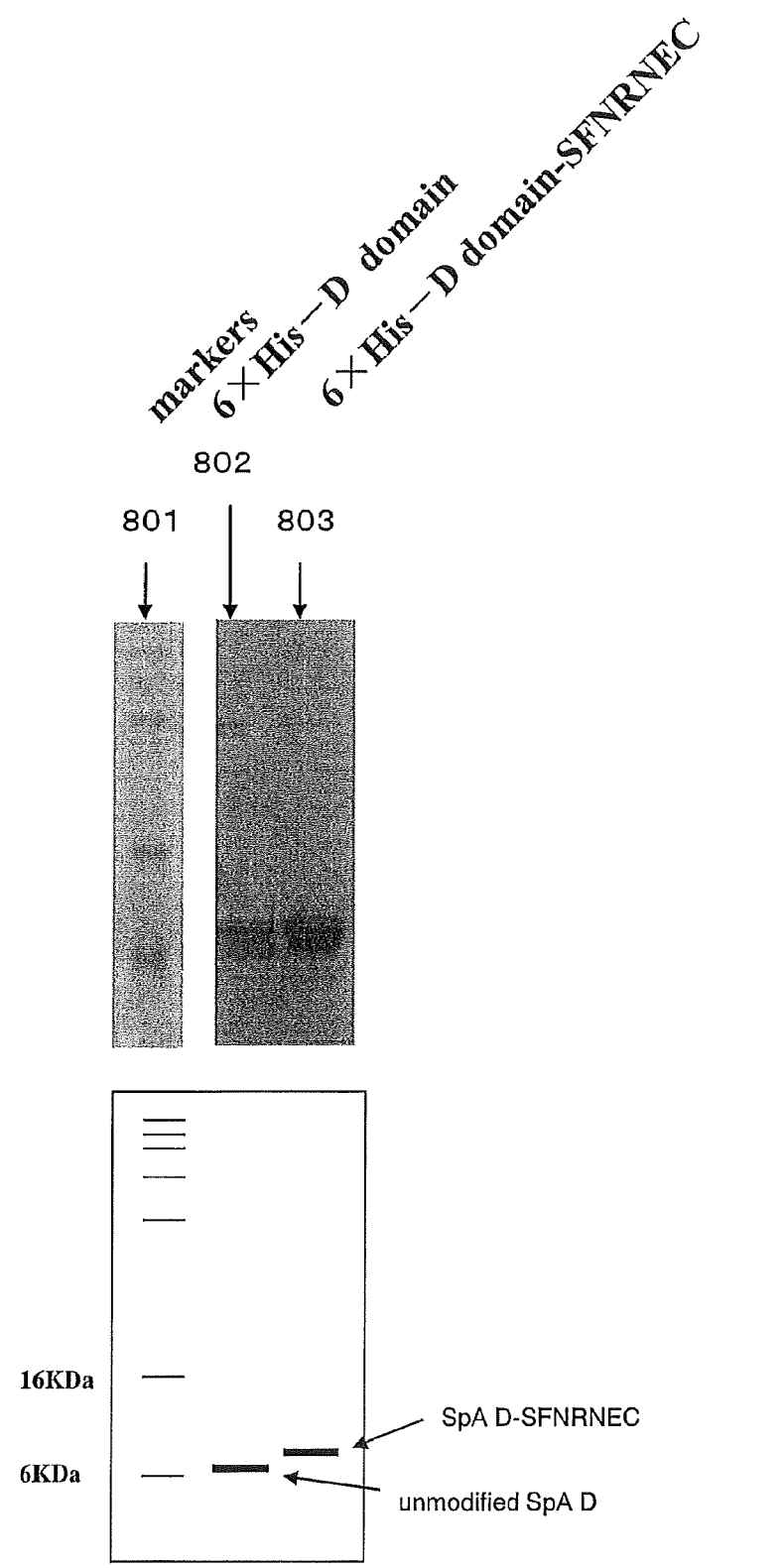
FIG. 8 is a photograph of the electrophoresis showing the amplification of the SF-modified D domain.

In FIG. 8, reference number 801 indicates the plural bands which were formed of markers each having different molecular weights. Reference number 803 indicates the band of the SF-modified D domain. Reference number 802 indicates the band of D domain (hereinafter "C-modified D domain"), which was obtained in accordance with the process similar to the above process except that one molecule of cysteine was modified at the C-terminal thereof in place of the SF-modification, as shown in FIG. 10.

As understood from FIG. 8, there is a difference between band 802 and band 803. The band 803 demonstrates the SF-modified D domain was obtained.

Thus, obtained was the SF-modified D domain 901 comprising the N-terminal modified with 6×His and the C-terminal modified with the amino acid sequence SFNRNEC. The term "6×His" is omitted for the sake of shorthand as long as it is not required. Accordingly, the term "SF-modified D domain" means the SF-modified D domain 901 shown in FIG. 9. Similarly, the term "C-modified D domain" means the C-modified domain 902 shown in FIG. 10.

(Confirmation of the Effect of Suppressing the Formation of Disulfide Bond with SEQ ID: 1)

Figure 11:
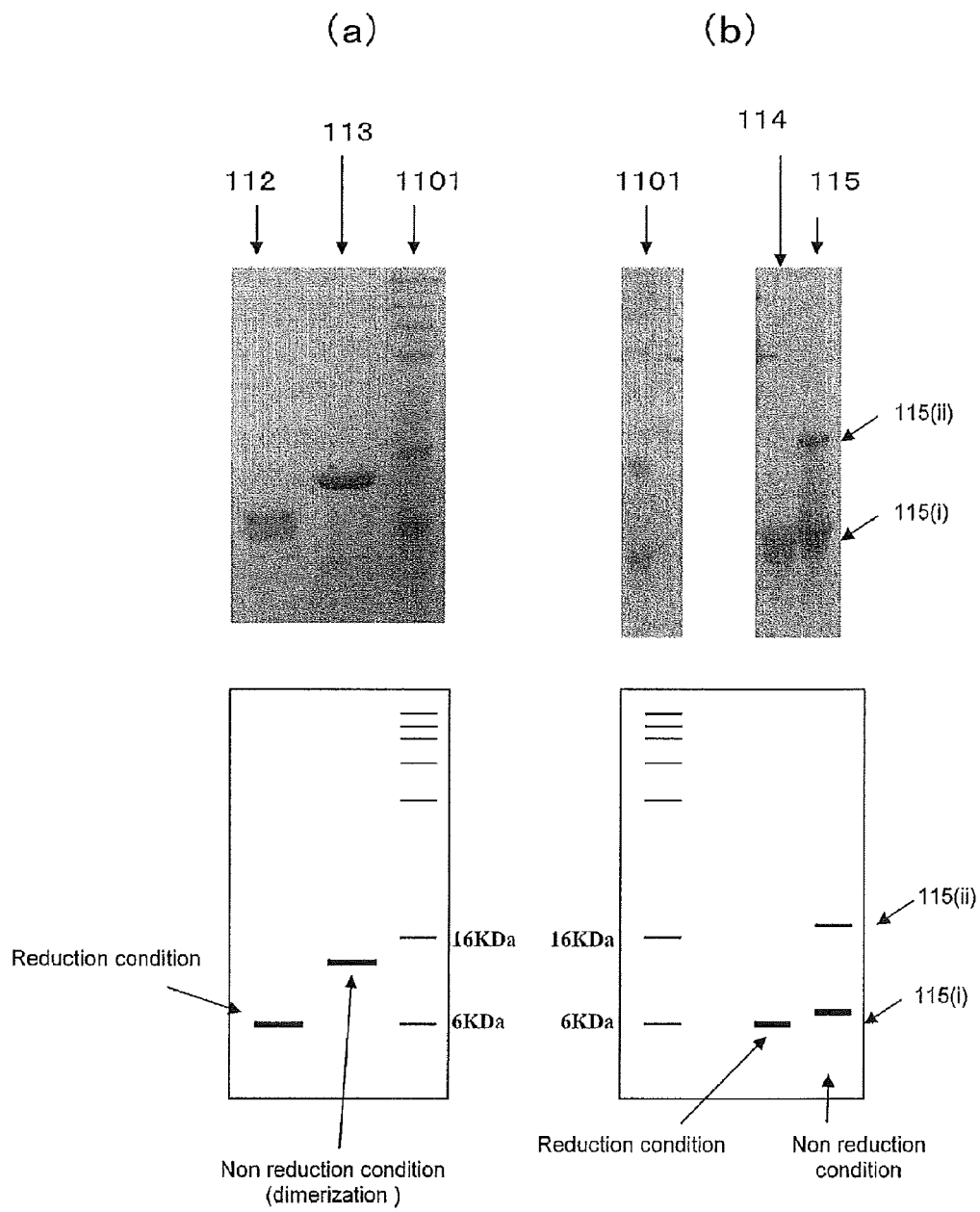
FIG. 11(a) is a photograph of the electrophoresis when the molecular weights of the C-modified D domain in the reduction condition and the non-reduction condition are measured with SDS-PAGE.
FIG. 11(b) is a photograph of the electrophoresis when the molecular weights of the SF-modified D domain in the reduction condition and the non-reduction condition are measured with SDS-PAGE.

FIG. 11(*a*) shows a photograph of the electrophoresis with which the molecular weight of C-modified D domain in the reduction condition and non-reduction condition was measured with the use of SDS-PAGE.

FIG. 11(*b*) shows a photograph of the electrophoresis with which the molecular weight of SF-modified D domain in the reduction condition and non-reduction condition was measured with the use of SDS-PAGE.

The reduction condition means a condition under which reduction of disulfide bond is promoted, thus a mercapto group is generated. Namely, dimerization is suppressed under the reduction condition.

The non-reduction condition means a condition under which oxidization of mercapto group is not prohibited. Namely, dimerization is promoted under the non-reduction condition.

The reduction condition and non-reduction condition were obtained in the following processes.

The SF-modified D domain at amount of 5 μg was added to 500 μL of PBS buffer (pH: 7.4) to obtain a solution with non-reduction condition.

Next, the method to obtain the reduction condition is described below. First, dithiothreitol (hereinafter, "DTT") was added to the solution so that the final concentration thereof was 5 mM. Subsequently, the solution was stirred slowly overnight at a temperature of 4° C. Furthermore, using PD-10(available from GE Healthcare Company), the PBS buffer was substituted with PBS including 1 mM EDTA (pH: 6.8) to obtain the reduction condition. EDTA is abbreviated name of ethylenediaminetetraacetic acid, and it inhibits the activity of metalloprotease. Similar process was used for the C-modified D domain.

In FIG. 11(a), reference number 112 indicates the band of the C-modified D domain in the reduction condition. Reference number 113 indicates the band in the non-reduction condition. Reference number 1101 indicates the plural bands which were formed of markers each having different molecular weights.

As understood from FIG. 11(a), a disulfide bond is formed between two cysteines in the non-reduction condition, and two C-modified D domains are bound. Needless to say, this means that dimerization was caused.

In FIG. 11(b), reference number 114 indicates the band of the SF-modified D domain in the reduction condition. Reference number 115 indicates the band of the SF-modified D domain in the non-reduction condition.

Bands 115(i) and 115(ii) were observed in non-reduction condition column in FIG. 11(b). Band 115(i) indicates SF-modified D domain. In the SF-modified D domain, a sulfur atom contained in cysteine does not form a disulfide bond with one another. Band 115 (ii) indicates dimerized SF-modified D domain. Band 115 (i) is much stronger than Band 115(ii).

As understood from FIG. 11(b), even in the non-reduction condition, an amount of the monomeric D domain which fails to form disulfide bonds, is greater than an amount of the dimmers of two D domains which are bound through disulfide bond. This means that the amino acid sequence represented by SEQ ID:1 suppresses the dimerization through disulfide bond.

(Method for Immobilizing D Domain on the Surface of a Substrate)

In the method for immobilizing the D domain on the surface of a substrate, a sensor chip CM5 (available from GE Health Company) was used. The sensor chip CM 5 was a substrate with a surface on which dextran was immobilized, the dextran being added to carboxyl groups in high density. The amount of D domain immobilized on the sensor chip CM 5 was measured with the use of BioCORE2000 (available from GE Healthcare Company).

Comparative Example 1

Amine-Coupling Method

First, prepared was a mixture containing 0.05M N-hydroxysuccinimide (hereinafter, "NHS") and 0.2M N-ethyl-N'-(3-dimethylaminopropyl)carbodiimide hydrochloride (hereinafter, "EDS"). The mixture was added to the surface of a sensor chip CM5 (available from GE Healthcare Company) for two minutes at a flow rate of 5 mL/min. Thus, the carboxyl group was substituted with the NHS ester.

Furthermore, the C-modified D domain was added under the condition of pH 4.5. The NHS ester was substituted with the $-NH_2$ group (epsilon-amino group) in lysine residue which is included in the D domain, and the D domain was immobilized via the amide bond. The procedure was performed until the predetermined immobilization amount was obtained, while the immobilization amount was monitored with the use of BiaCORE2000 (available from GE Healthcare Company).

Finally, ethanol amine was added for four minutes at a flow rate of 5 μL/minute. Thus, unreacted carboxyl groups were inactivated.

Figure 12:
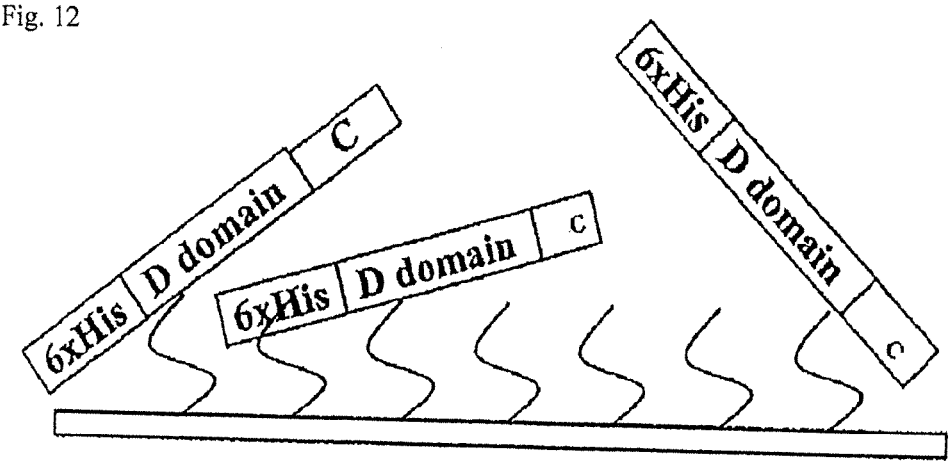
FIG. 12 shows schematically how the C-modified D domain is immobilized on the sensor chip CM5.

FIG. 12 shows schematically how the C-modified D domain is immobilized on the sensor chip CM5.

The dashed line in FIG. 14 shows the measurement result of the immobilization amount of the C-modified D domain measured with BiaCORE2000 (available from GE Healthcare Company), after the antibody mouse IgG1 (200 nm) at an amount of 880 RU (approximately 880 nm/mm$^2$) was bound to C-modified D domain immobilized on the substrate.

The dashed line in FIG. 15 shows the measurement result of the immobilization amount of the C-modified D domain measured with BiaCORE2000 (available from GE Healthcare Company), after the antibody mouse IgG2a (200 nm) at an amount of 880 RU (approximately 880 nm/mm$^2$) was bound to C-modified D domain immobilized on the substrate.

Example 1

Thiol-Coupling Method

Similarly to the comparative example 1, the mixture containing 0.05M NHS and 0.2M EDC was added to the surface of the sensor chip CM5. Thus, the carboxyl group was substituted with the NHS ester.

Next, as shown in FIG. 1, pH8.5 80 mM PDEA (2-(2-pyridinyldithio) ethaneamine hydrochloride) was added for four minutes with flow rate of 5 μL/minute. Thus, the NHS ester was substituted with disulfide.

Furthermore, the SF-modified D domain was added under condition of pH 4.5. Thus, the SF-modified D domain was immobilized on the surface of the substrate as shown in the following chemical formula (III).

[Chem.3]

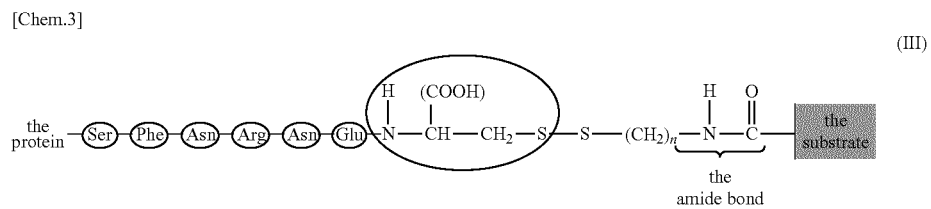

(III)

The procedure was performed until the predetermined immobilization amount was obtained similarly to the comparative example 1, while the immobilization amount was monitored with the use of BiaCORE2000 (available from GE Healthcare Company).

Finally, pH 4.3 50 mM cystamine/1M NaCl were added for four minutes with flow rate of 5 μL/min. Thus, unreacted carboxyl groups were inactivated.

Figure 13:
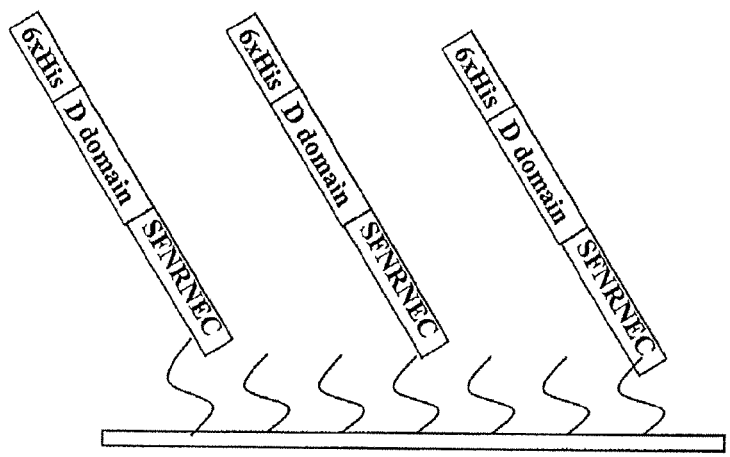
FIG. 13 shows schematically how the SF-modified D domain is immobilized on the sensor chip CM5.

FIG. 13 shows schematically how the SF-modified D domain is immobilized on the sensor chip CM5.

The contiuous line in FIG. 14 shows the measurement result of the immobilization amount of the SF-modified D domain measured with the use of BiaCORE2000 (available from GE Healthcare Company), after the antibody mouse IgG1 (200 nm) at an amount of 880 RU (approximately 880 nm/mm²) was bound to SF-modified D domain immobilized on the substrate.

The continuous line in FIG. 15 shows the measurement result of the immobilization amount of the SF-modified D domain measured with the use of BiaCORE2000 (available from GE Healthcare Company), after the antibody mouse IgG2a (200 nm) at a amount of 960 RU (approximately 960 nm/mm²) was bound to SF-modified D domain immobilized on the substrate.

Both of FIG. 14 and FIG. 15 reveal that the amount of D domain immobilized with thiol-couping method (continuous line) is greater than the amount of D domain immobilized with use of amine-coupling method (dashed line). Presumably, the D domain fails to be oriented uniformly with use of amine-coupling method, whereas the SF-modified D domain is oriented uniformly with use of thiol-coupling method, as shown in FIG. 12 and FIG. 13.

Example 2

In the example 2, the amino acid sequence of SEQ ID:1 was modified at the C-terminal of Protein A, which has all of the A to E domains, as shown in FIG. 16. The N-terminal of the Protein A was modified with 6×His).

Similar experiment to the example 1 and the comparative example 1 was performed, except that the following gene (SEQ ID:6) was used, which coded for Protein A having all of the A to E domains.

```
ATGCTGACTTTACAAATACATACAGGGGGTATTAATTTGAAAAAGAAAAACAT
TTATTCAATTCGTAAACTAGGTGTAGGTATTGCATCTGTAACTTTAGGTACATTACTTATA
TCTGGTGGCGTAACACCTGCTGCAAATGCTGCGCAACACGATGAAGCTCAACAAAAT
GCTTTTTATCAAGTCTTAAATATGCCTAACTTAAATGCTGATCAACGCAATGGTTTTATC
CAAAGCCTTAAAGATGATCCAAGCCAAAGTGCTAACGTTTTAGGTGAAGCTCAAAAA
CTTAATGACTCTCAAGCTCCAAAAGCTGATGCGCAACAAAATAACTTCAACAAAGATC
AACAAAGCGCCTTCTATGAAATCTTGAACATGCCTAACTTAAACGAAGCGCAACGTAA
CGGCTTCATTCAAAGTCTTAAAGACGACCCAAGCCAAAGCACTAACGTTTTAGGTGA
AGCTAAAAAATTAAACGAATCTCAAGCACCGAAAGCTGATAACAATTTCAACAAAGA
ACAACAAAATGCTTTCTATGAAATCTTGAATATGCCTAACTTAAACGAAGAACAACGC
AATGGTTTCATCCAAAGCTTAAAAGATGACCCAAGCCAAAGTGCTAACCTATTGTCAG
AAGCTAAAAAGTTAAATGAATCTCAAGCACCGAAAGCGGATAACAAATTCAACAAAG
AACAACAAAATGCTTTCTATGAAATCTTACATTTACCTAACTTAAACGAAGAACAACG
CAATGGTTTCATCCAAAGCCTAAAAGATGACCCAAGCCAAAGCGCTAACCTTTTAGCA
GAAGCTAAAAAGCTAAATGATGCTCAAGCACCAAAAGCTGACAACAAATTCAACAAA
GAACAACAAAATGCTTTCTATGAAATTTTACATTTACCTAACTTAACTGAAGAACAAC
GTAACGGCTTCATCCAAAGCCTTAAAGACGATCCTTCAGTGAGCAAAGAAATTTTAGC
AGAAGCTAAAAAGCTAAACGATGCTCAAGCACCAAAAGAGGAAGACAATAACAAGC
CTGGCAAAGAAGACAATAACAAGCCTGGCAAAGAAGACAACAACAAGCCTGGTAAA
GAAGACAACAACAAGCCTGGTAAAGAAGACAACAACAAGCCTGGCAAAGAAGACA
ATAACAAGCCTGGTAAAGAAGACAACAAAAAACCTGGTAAAGAAGATGGCAACAAG
CCTGGTAAAGAAGACAACAAAAAACCTGGTAAAGAAGACGGCAACAAGCCTGGCAA
AGAAGATGGCAACAAACCTGGTAAAGAAGATGGTAACGGAGTACATGTCGTTAAACC
TGGTGATACAGTAAATGACATTGCAAAAGCAAACGGCACTACTGCTGACAAAATTGCT
GCAGATAACAAATTAGCTGATAAAAACATGATCAAACCTGGTCAAGAACTTGTTGTTG
ATAAGAAGCAACCAGCAAACCATGCAGATGCTAACAAAGCTCAAGCATTACCAGAAA
```

-continued

```
CTGGTGAAGAAAATCCATTCATCGGTACAACTGTATTTGGTGGATTATCATTAGCCTTA

GGTGCAGCGTTATTAGCTGGACGTCGTCGCGAACTATAA
```

Figure 17:
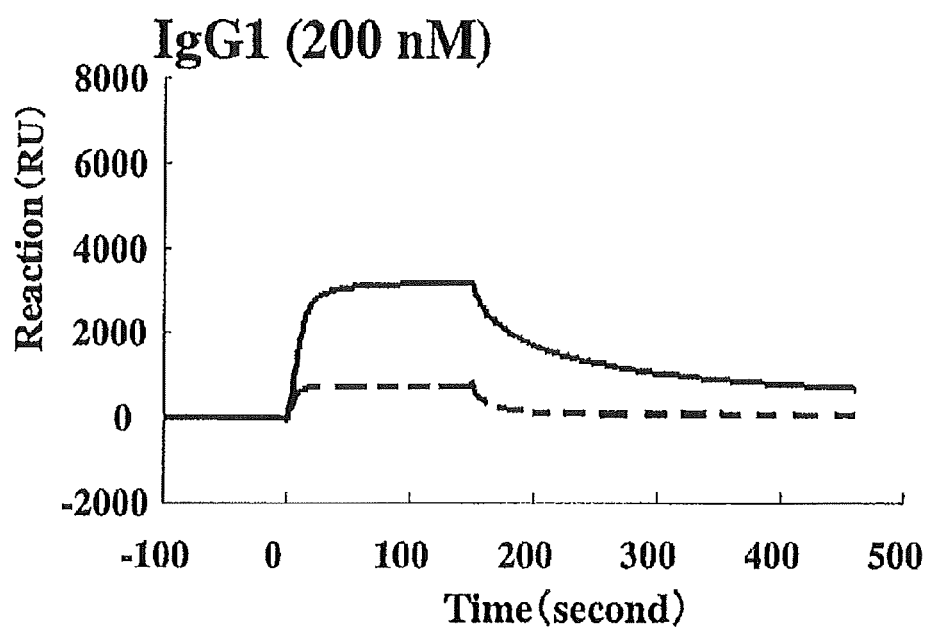
FIG. 17 shows a graph showing the measurement results of the immobilization amounts of the C-modified SpA and the SF-modified SpA.

The dashed line in FIG. 17 shows the measurement result of the immobilization amount of the C-modified SpA which was measured with the use of BiaCORE2000 (available from GE Healthcare Company), after the antibody mouse IgG1 (200 nm) at an amount of 880 RU (approximately 880 nm/mm$^2$) had been bound to C-modified SpA immobilized on the substrate.

Figure 18:
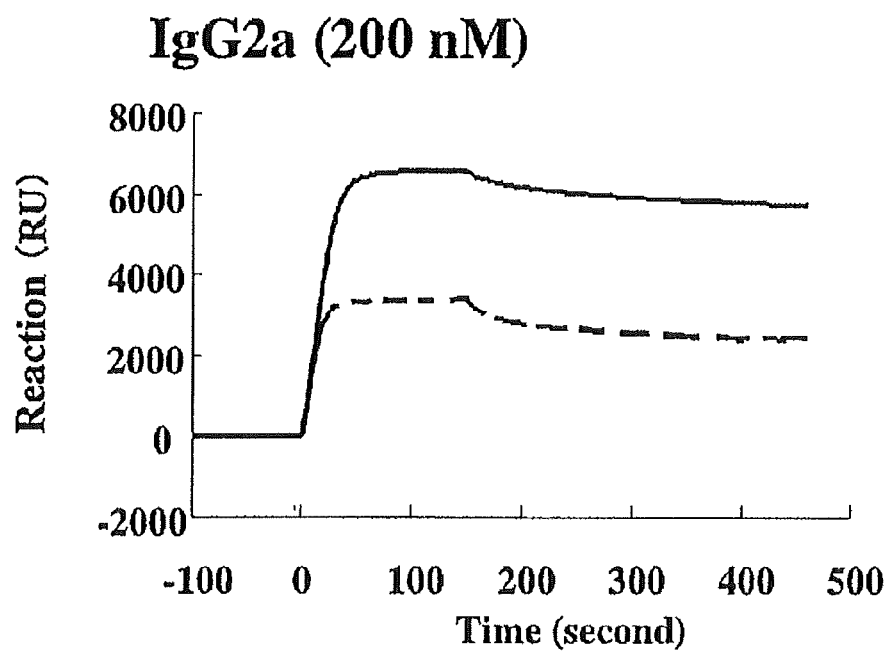
FIG. 18 shows a graph showing the measurement results of the immobilization amounts of the C-modified SpA and the SF-modified SpA.

The dashed line in FIG. 18 shows the measurement result of the immobilization amount of the C-modified SpA which was measured with the use of BiaCORE2000 (available from GE Healthcare Company), after the antibody mouse IgG2a (200 nm) at an amount of 880 RU (approximately 880 nm/mm$^2$) had been bound to C-modified SpA immobilized on the substrate.

The solid line in FIG. 17 shows the measurement result of the immobilization amount of the SF-modified SpA which was measured with the use of BiaCORE2000 (available from GE Healthcare Company), after the antibody mouse IgG1 (200 nm) at an amount of 960 RU (approximately 960 nm/mm$^2$) had been bound to SF-modified SpA immobilized on the substrate.

The solid line in FIG. 18 shows the measurement result of the immobilization amount of the SF-modified SpA which was measured with the use of BiaCORE2000 (available from GE Healthcare Company), after the antibody mouse IgG2a (200 nm) at a amount of 960 RU (approximately 960 nm/mm$^2$) had been bound to SF-modified SpA immobilized on the substrate.

Both of FIG. 17 and FIG. 18 reveal that the amount of the SpA immobilized with thiol-couping method (continuous line) is greater than the amount of the SpA immobilized with use of amine-coupling method (dashed line). Presumably, the SpA fails to be oriented uniformly with amine-coupling method, whereas the SF-modified SpA is oriented uniformly with use of thiol-coupling method, similarly to the example 1.

INDUSTRIAL APPLICABILITY

The present invention may be used to fabricate a sensor comprising the protein on the surface thereof.

REFERENCE SIGNS LIST

201: Cloning vector for the confirmation of formation of SF-modified D domain gene
301: Vector for the expression of the SF-modified D domain gene with *E. Coli*
801: Band formed by a plurality of markers with different molecular weights
802: Band of the C-modified D domain
803: Band of the SF-modified D domain
112: Band of C-modified D domain in the reduction condition
113: Band of C-modified D domain in the non-reduction condition
1101: Band formed by a plurality of markers with different molecular weights
114: Band of SF-modified D domain in the reduction condition
115: Band of SF-modified D domain in the non-reduction condition

---

The invention claimed is:

1. A method for binding a protein to a surface of a substrate, the method comprising the following steps (A) to (C):
 (A) preparing said substrate with the surface represented by the following chemical formula:

$$\text{Pyridine—S—S—(CH}_2)_n\text{—N(H)—C(=O)—The Substrate}$$

wherein n represents an integer within the range of 2 to 20;
 (B) supplying a solution containing said protein to the surface,
 wherein said protein consists of a D domain of a Protein A, and
 a C-terminal of said D domain of said Protein A is linked to the serine residue of an amino acid sequence represented by SEQ ID NO:1 (SFNRNEC); and
 (C) binding the cysteine residue of the amino acid sequence represented by SEQ ID NO:1 to the surface of said substrate.

2. The method of claim 1, wherein said surface is bound to said protein according to the following chemical formula (III) after step (C):

$$\text{(III)}$$

wherein n denotes an integer within the range of 2 to 20.

3. The method of claim 1, wherein step (A) comprises the following steps (i) to (ii) in this order:
 (i) reacting 1-ethyl-3-(3-dimethylaminopropyl)carbodiimide HCl or equivalent thereof and N-hydroxysuccinimide with a carboxyl group on the surface of said substrate, and
 (ii) reacting a compound represented by following formula (IV) with the carboxyl group modified in the step (i)

$$\text{Pyridine—S—S—(CH}_2)_n\text{—NH}_3^+\text{X}^- \quad \text{(IV)}$$

wherein n denotes an integer within the range of 2 to 20, and X represents a halogen atom.

4. The method of claim 3, wherein n in formula (IV) is 2.

5. A method for binding a protein to a surface of a substrate, the method comprising the following steps (A) to (C):
 (A) preparing said substrate with the surface represented by the following chemical formula:

$$\text{Pyridine—S—S—(CH}_2)_n\text{—N(H)—C(=O)—The Substrate}$$

wherein n represents a natural number within the range of 2 to 20;
 (B) supplying a solution containing said protein to the surface,
 wherein said protein consists of a Protein A, and
 a C-terminal of said Protein A is linked to the serine residue of an amino acid sequence represented by SEQ ID NO: 1 (SFNRNEC); and
 (C) binding the cysteine residue of the amino acid sequence represented by SEQ ID NO:1 to the surface of said substrate.

6. The method of claim 5, wherein said surface is bound to said protein according to the following chemical formula (III) after step (C):

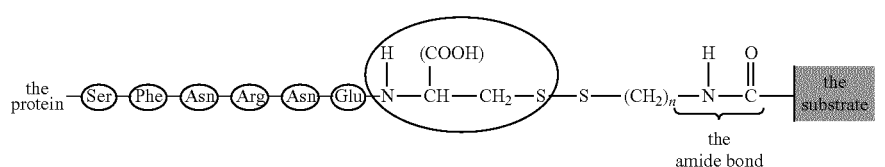

(III)

wherein n denotes an integer within the range of 2 to 20.

7. The method of claim 5, wherein step (A) comprises the following steps (i) to (ii) in this order:
   (i) reacting 1-ethyl-3-(3-dimethylaminopropyl)carbodiimide HCl or equivalent thereof and N-hydroxysuccinimide with a carboxyl group on the surface of said substrate, and
   (ii) reacting a compound represented by following formula (IV) with the carboxyl group modified in the step (i)

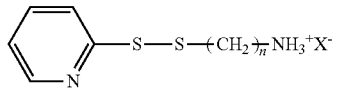

(IV)

wherein n denotes a natural number within the range of 2 to 20, and X represents a halogen atom.

8. The method of claim 7, wherein n in formula (IV) is 2.

* * * * *

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial
<220> FEATURE:
<223> OTHER INFORMATION: Amino Acid Sequence modified with Protein A to
      prevent from causing dimer

<400> SEQUENCE: 1

Ser Phe Asn Arg Asn Glu Cys
1               5

<210> SEQ ID NO 2
<211> LENGTH: 183
<212> TYPE: DNA
<213> ORGANISM: Staphylococcus aureus

<400> SEQUENCE: 2
gctgatgcgc aacaaaataa cttcaacaaa gatcaacaaa gcgccttcta tgaaatcttg      60
aacatgccta acttaaacga agcgcaacgt aacggcttca ttcaaagtct taaagacgac     120
ccaagccaaa gcactaacgt tttaggtgaa gctaaaaaat taaacgaatc tcaagcaccg     180
aaa                                                                   183
```

<210> SEQ ID NO 3
<211> LENGTH: 21
<212> TYPE: DNA
<213> ORGANISM: Artificial
<220> FEATURE:
<223> OTHER INFORMATION: DNA sequence for coding an Amino Acid Sequence modified with Protein A to prevent from causing dimer

<400> SEQUENCE: 3
agcttcaacc gtaacgaatg c                                              21

<210> SEQ ID NO 4
<211> LENGTH: 28
<212> TYPE: DNA
<213> ORGANISM: Artificial
<220> FEATURE:
<223> OTHER INFORMATION: Primer P1 modified with DNA sequence coding restriction enzyme site NdeI at the N-terminal thereof

<400> SEQUENCE: 4
atcatatggc cgatgcgcaa caaaataa                                       28

<210> SEQ ID NO 5
<211> LENGTH: 49
<212> TYPE: DNA
<213> ORGANISM: Artificial
<220> FEATURE:
<223> OTHER INFORMATION: Primer P2 coding DNA sequence coding SEQ_ID:02-stop_codon-restriction enzyme site XhoI

<400> SEQUENCE: 5
atctcgagtt attagcattc gttacggttg aagcttttyg gwgcttgwg                49

<210> SEQ ID NO 6
<211> LENGTH: 1587
<212> TYPE: DNA
<213> ORGANISM: Staphylococcus aureus

<400> SEQUENCE: 6
atgctgactt tacaaataca tacagggggt attaatttga aaagaaaaa catttattca      60
attcgtaaac taggtgtagg tattgcatct gtaactttag gtacattact tatatctggt    120
ggcgtaacac ctgctgcaaa tgctgcgcaa cacgatgaag ctcaacaaaa tgctttttat    180
caagtcttaa atatgcctaa cttaaatgct gatcaacgca atggttttat ccaaagcctt    240
aaagatgatc caagccaaag tgctaacgtt ttaggtgaag ctcaaaaact taatgactct    300
caagctccaa aagctgatgc gcaacaaaat aacttcaaca agatcaaca aagcgccttc    360
tatgaaatct gaacatgcc taacttaaac gaagcgcaac gtaacggctt cattcaaagt    420
cttaaagacg acccaagcca agcactaacg tttttaggtg aagctaaaaa attaaacgaa    480
tctcaagcac cgaaagctga taacaatttc aacaagaac aacaaaatgc tttctatgaa    540
atcttgaata tgcctaactt aaacgaagaa caacgcaatg gtttcatcca agcttaaaa    600
gatgacccaa gccaaagtgc taacctattg tcagaagcta aaagttaaa tgaatctcaa    660
gcaccgaaag cggataacaa attcaacaaa gaacaacaaa atgctttcta tgaaatctta    720
catttaccta acttaaacga agaacaacgc aatggtttca tccaaagcct aaaagatgac    780
ccaagccaaa gcgctaacct tttagcagaa gctaaaaagc taaatgatgc tcaagcacca    840
aaagctgaca caaattcaa caagaacaca caaaatgctt tctatgaaat tttcatttta    900
cctaacttaa ctgaagaaca acgtaacggc ttcatccaaa gcttaaaga cgatccttca    960
gtgagcaaag aaatttttagc agaagctaaa aagctaaacg atgctcaagc accaaaagag   1020

```
gaagacaata acaagcctgg caaagaagac aataacaagc ctggcaaaga agacaacaac    1080
aagcctggta aagaagacaa caacaagcct ggtaaagaag acaacaacaa gcctggcaaa    1140
gaagacaata acaagcctgg taaagaagac aacaaaaaac ctggtaaaga agatggcaac    1200
aagcctggta aagaagacaa caaaaaacct ggtaaagaag acggcaacaa gcctggcaaa    1260
gaagatggca acaaacctgg taaagaagat ggtaacggag tacatgtcgt taaacctggt    1320
gatacagtaa atgacattgc aaaagcaaac ggcactactg ctgacaaaat tgctgcagat    1380
aacaaattag ctgataaaaa catgatcaaa cctggtcaag aacttgttgt tgataagaag    1440
caaccagcaa accatgcaga tgctaacaaa gctcaagcat taccagaaac tggtgaagaa    1500
aatccattca tcggtacaac tgtatttggt ggattatcat tagccttagg tgcagcgtta    1560
ttagctggac gtcgtcgcga actataa                                        1587
```